(12) United States Patent
Eisinger

(10) Patent No.: US 11,622,767 B2
(45) Date of Patent: Apr. 11, 2023

(54) SEALED TROCAR ASSEMBLY FOR STAPLING DEVICE

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 156 days.

(21) Appl. No.: 17/151,796

(22) Filed: Jan. 19, 2021

(65) Prior Publication Data
US 2021/0251632 A1  Aug. 19, 2021

Related U.S. Application Data

(60) Provisional application No. 62/978,339, filed on Feb. 19, 2020.

(51) Int. Cl.
*A61B 17/115* (2006.01)
*A61B 17/34* (2006.01)

(52) U.S. Cl.
CPC .......... *A61B 17/1155* (2013.01); *A61B 17/34* (2013.01)

(58) Field of Classification Search
CPC .............. A61B 17/1155; A61B 17/105; A61B 17/1114; A61B 17/34
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report from Appl. No. 14181908.6 dated May 26, 2015.

(Continued)

*Primary Examiner* — Nathaniel C Chukwurah
(74) *Attorney, Agent, or Firm* — Carter, DeLuca & Farrell LLP

(57) ABSTRACT

A stapling device includes a handle assembly and an adaptor assembly extending from the handle assembly and including a sealed trocar assembly. The trocar assembly includes a trocar housing defining a lumen, an annular seal having an inner annular surface defining an inner opening, and a trocar disposed within the lumen of the trocar housing, through the inner opening of the annular seal, and movable through the lumen of the trocar and the inner opening of the annular seal, and a seal retainer operably coupled to the trocar housing and the annular seal. The trocar includes an elongate body portion having a distal end and a trocar member extending distally from the distal end of the elongate body portion.

20 Claims, 6 Drawing Sheets

(56) References Cited

U.S. PATENT DOCUMENTS

| | | |
|---|---|---|
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshln et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,714 A * | 2/1999 | Danks ............... A61B 17/3462 |
| | | 604/167.03 |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 5,993,471 A * | 11/1999 | Riza ............... A61B 17/3498 |
| | | 606/185 |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | |
|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |

(56) References Cited

U.S. PATENT DOCUMENTS

| | | |
|---|---|---|
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 | 7/2014 | Shelton, IV et al. |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 | 1/2016 | Zingman |
| 9,289,207 B2 | 3/2016 | Shelton, IV |
| 9,301,763 B2 | 4/2016 | Qiao et al. |
| 9,307,994 B2 | 4/2016 | Gresham et al. |

(56) References Cited

U.S. PATENT DOCUMENTS

| | | |
|---|---|---|
| 9,326,773 B2 | 5/2016 | Casasanta, Jr. et al. |
| 9,351,729 B2 | 5/2016 | Orban, III et al. |
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 | 10/2016 | Swayze et al. |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 | 3/2017 | Swayze et al. |
| 9,597,082 B2 | 3/2017 | Stokes et al. |
| 9,603,599 B2 | 3/2017 | Miller et al. |
| 9,629,624 B2 | 4/2017 | Hessler et al. |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 | 3/2019 | DiNardo et al. |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0284370 A1 | 9/2014 | Sahin |
| 2015/0083772 A1 | 3/2015 | Miller et al. |

(56) References Cited

U.S. PATENT DOCUMENTS

| | | |
|---|---|---|
| 2015/0173763 A1 | 6/2015 | Liu |
| 2015/0209045 A1 | 7/2015 | Hodgkinson et al. |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8401095 A1 | 3/1984 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |

OTHER PUBLICATIONS

European Examination Report from Appl. No. 14181908.6 dated May 3, 2016.

Extended European Search Report from corresponding Appl. No. 21157927.1 dated Apr. 15, 2021.

* cited by examiner

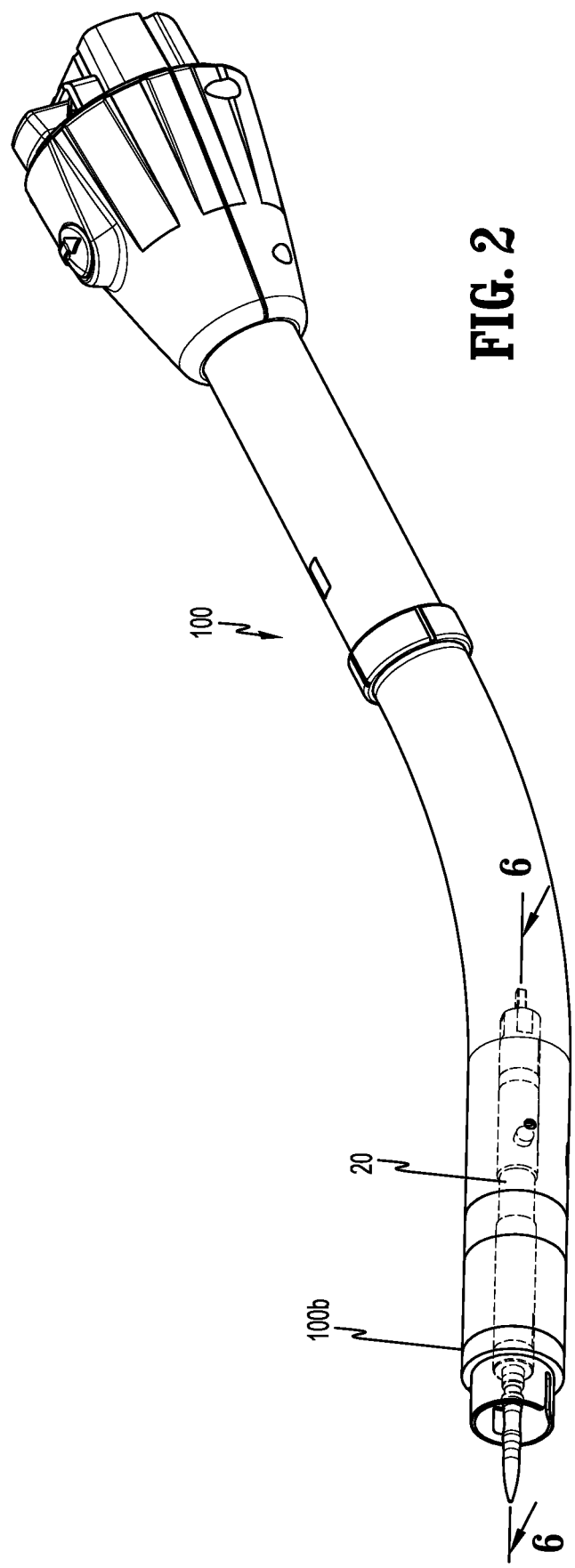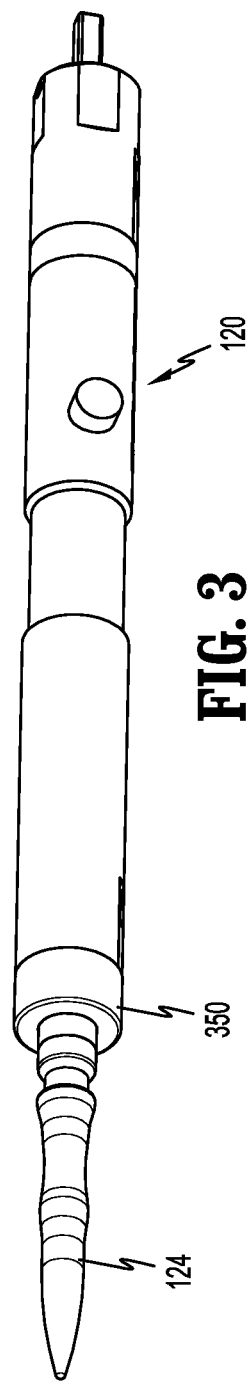

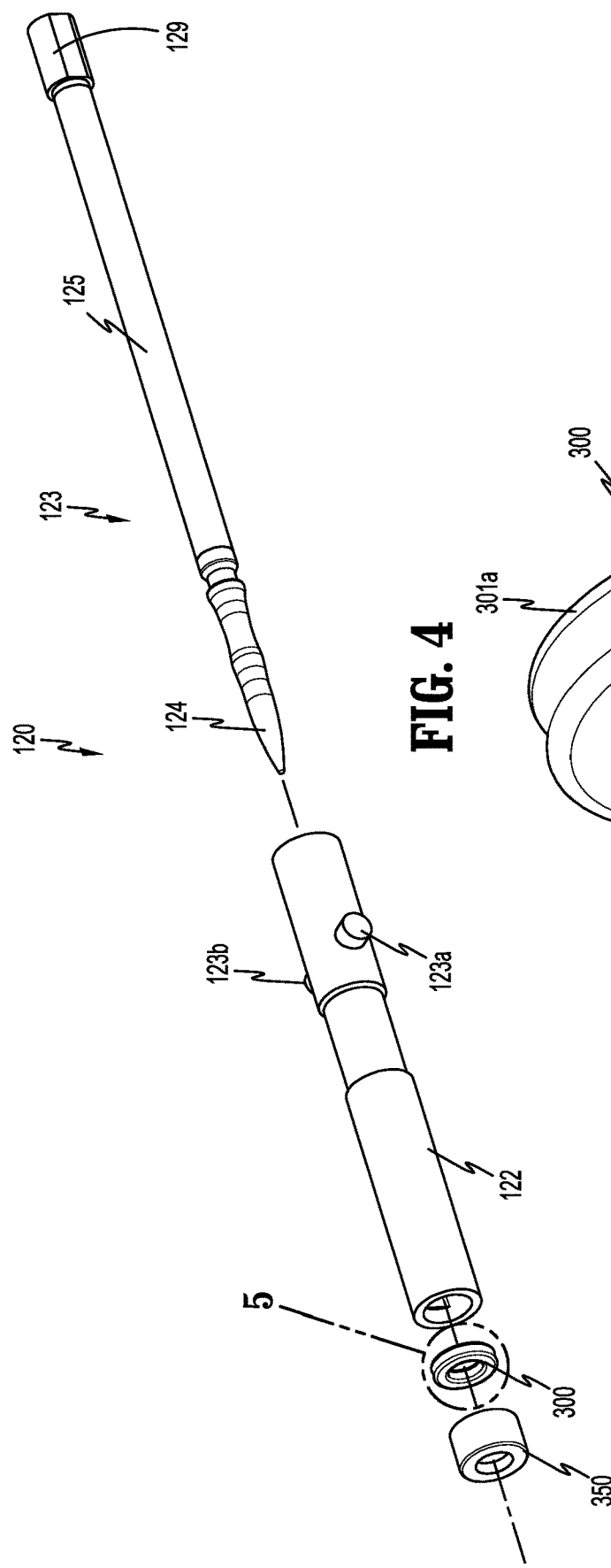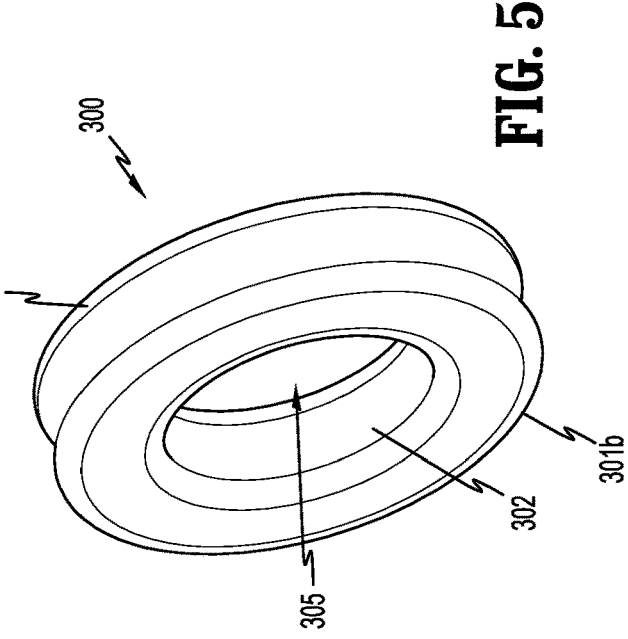

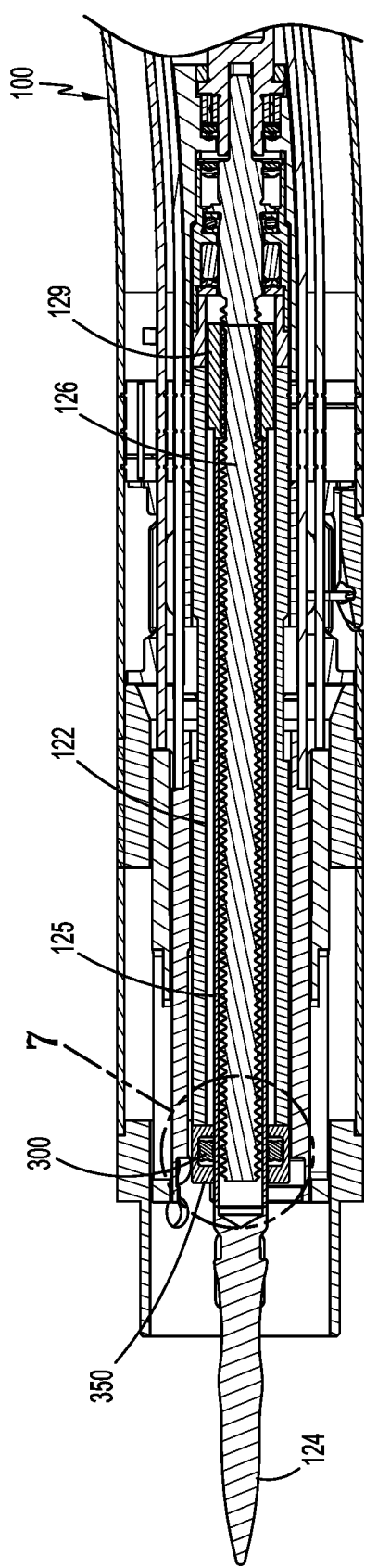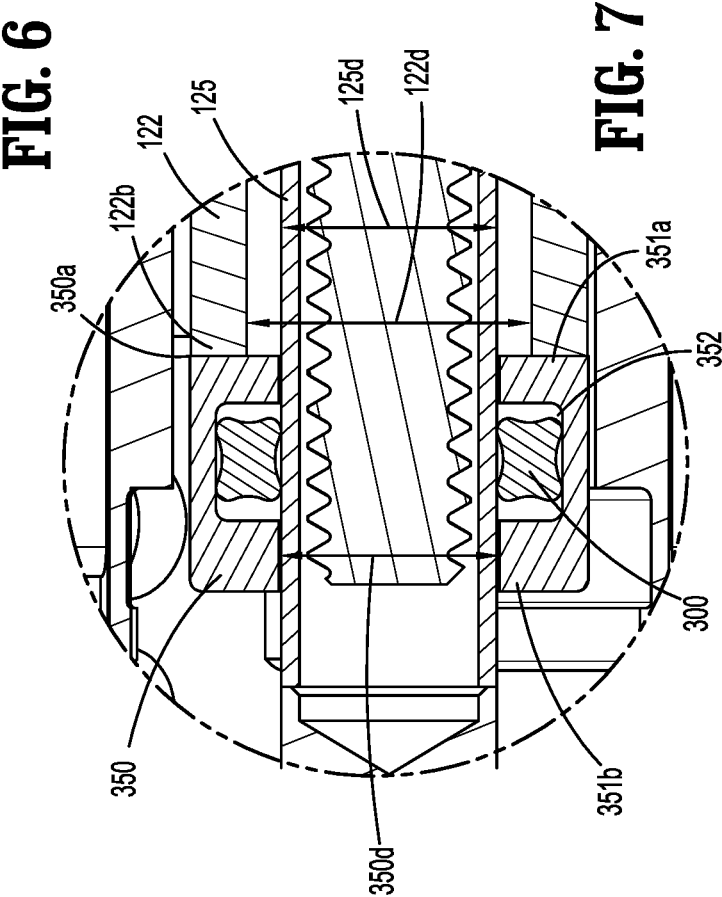

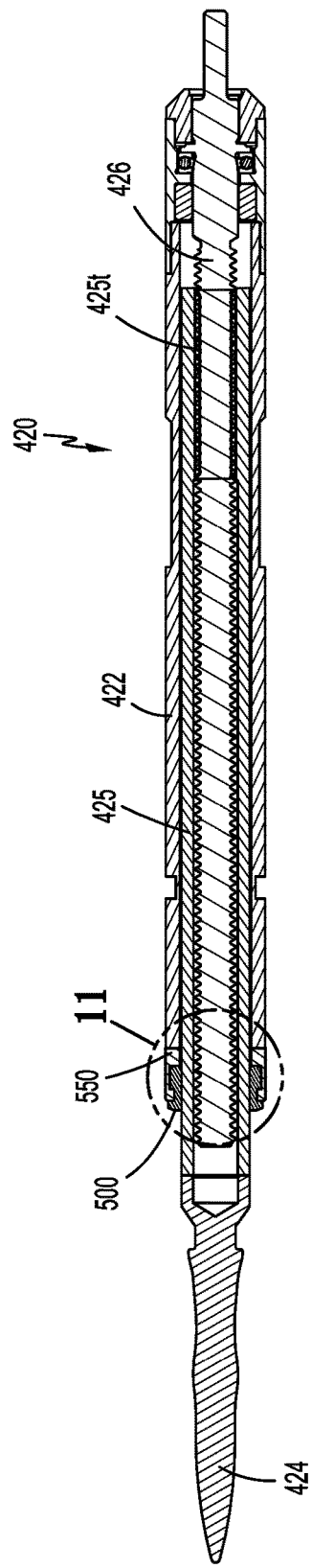
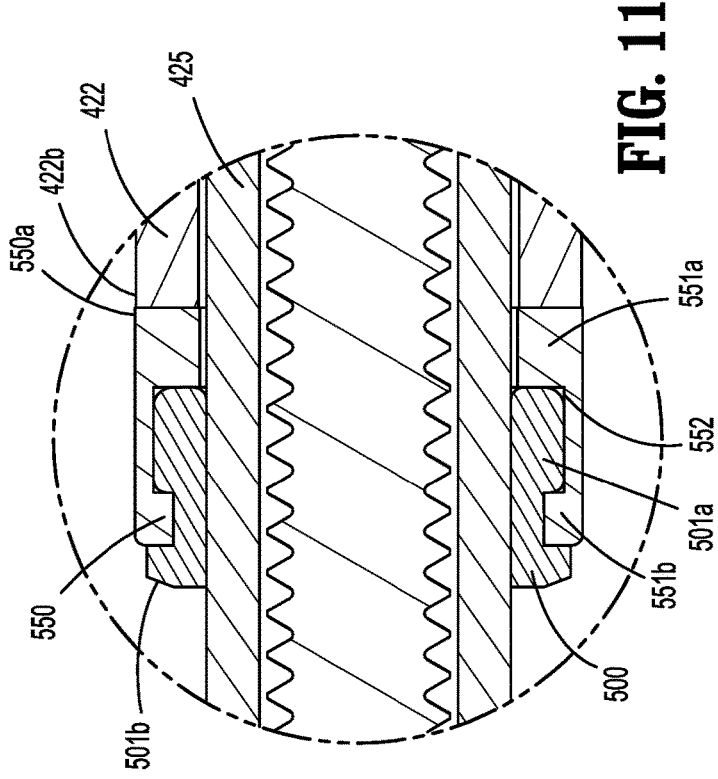
FIG. 10
FIG. 11

SEALED TROCAR ASSEMBLY FOR STAPLING DEVICE

CROSS-REFERENCE TO RELATED APPLICATIONS

This application claims the benefit of and priority to U.S. Provisional Patent Application Ser. No. 62/978,339 filed Feb. 19, 2020, the entire disclosure of which is incorporated by reference herein.

FIELD

This disclosure is generally related to surgical stapling devices and, more particularly, to surgical stapling devices and components for surgical stapling devices that include a sealed configuration.

BACKGROUND

Powered surgical stapling devices include a handle assembly, an adaptor assembly including a distal portion supported on the handle assembly, and a tool assembly (e.g., a staple cartridge) supported on the distal portion of the adaptor assembly. Some tool assemblies include a shell or reload assembly that has a staple cartridge, a staple pusher, and an annular knife. The staple cartridge supports one or more annular rows of staples, and the staple pusher is movable within the staple cartridge to eject the staples from the staple cartridge. The annular knife is positioned radially inward of the annular rows of staples and is movable from a retracted position to an advanced position to cut or core tissue. The annular knife can be movable simultaneously with the staple pusher or independently of the staple pusher to cut tissue during a surgical procedure, e.g., an anastomosis procedure.

In some applications, some components of the stapling device are disposable while others are reusable after proper sterilization. Proper sterilization of reusable components is more difficult and time consuming if contaminants flow into the adaptor assembly.

SUMMARY

This disclosure is directed to a surgical stapling device and to trocar assemblies of adaptor assemblies for surgical stapling devices that include a sealed configuration to prevent ingress of fluids therein.

In accordance with aspects of the disclosure, a stapling device includes a handle assembly and an adaptor assembly extending from the handle assembly. The adaptor assembly includes a trocar assembly disposed within the adaptor assembly. The trocar assembly includes a trocar housing including an inner surface defining a lumen, an annular seal positioned within the lumen of the trocar housing and having an inner annular surface defining an inner opening, and a trocar disposed within the lumen of the trocar housing, extending through the inner opening of the annular seal, and movable through the lumen of the trocar and the inner opening of the annular seal, and a seal retainer operably coupled to the trocar housing. The seal retainer is positioned to retain the annular seal within the lumen of the trocar housing. The trocar includes an elongate body portion having a distal end and a trocar member extending distally from the distal end of the elongate body portion.

In an aspect, the inner annular surface of the annular seal is frictionally engaged to the elongate body portion of the trocar to form a fluid-tight seal between the annular seal and the trocar.

In an aspect, the seal retainer is fixedly coupled to the trocar housing.

In an aspect, the trocar housing has a distal end and the seal retainer has a proximal end and the proximal end of the seal retainer is secured to the distal end of the trocar housing.

In an aspect, the seal retainer includes a proximal lip and a distal lip and defines an inner annular region between the proximal lip and the distal lip.

In an aspect, the annular seal is disposed within the inner annular region of the seal retainer.

In an aspect, the annular seal includes an outer surface having a proximal lip and a distal lip extending radially outwardly from the outer surface of the annular seal.

In an aspect, the proximal lip and the distal lip of the annular seal are disposed within the inner annular region of the seal retainer to prevent axial movement of the annular seal as the trocar moves through the inner opening of the annular seal.

In an aspect, the annular seal includes a recessed region defined between the proximal lip of the annular seal and the distal lip of the annular seal. The proximal lip of the annular seal may be disposed within the inner annular region of the seal retainer and the distal lip of the seal retainer may be disposed within the recessed region of the annular seal to prevent axial movement of the annular seal as the trocar moves through the inner opening of the annular seal.

In an aspect, the elongate body portion has an outer surface defining a non-circular shape and the inner opening of the annular seal is dimensioned to correspond in shape to the non-circular shape of the outer surface of the elongate body portion.

In an aspect, the annular seal is formed of an elastomeric material configured to compress when the trocar is positioned through the inner opening of the annular seal.

In accordance with aspects of the disclosure, a trocar assembly is provided including a trocar housing including an inner surface defining a lumen, an annular seal positioned within the lumen of the trocar housing and having an inner annular surface defining an inner opening, and a trocar disposed within the lumen of the trocar housing, extending through the inner opening of the annular seal, and movable through the lumen of the trocar and the inner opening of the annular seal, and a seal retainer operably coupled to the trocar housing. The seal retainer is positioned to retain the annular seal within the lumen of the trocar housing. The trocar includes an elongate body portion having a distal end and a trocar member extending distally from the distal end of the elongate body portion.

In an aspect, the inner annular surface of the annular seal is frictionally engaged to the elongate body portion of the trocar to form a fluid-tight seal between the annular seal and the trocar.

In an aspect, the seal retainer is fixedly coupled to the trocar housing.

In an aspect, the trocar housing has a distal end and the seal retainer has a proximal end and the proximal end of the seal retainer is secured to the distal end of the trocar housing.

In an aspect, the seal retainer includes a proximal lip and a distal lip and defines an inner annular region between the proximal lip and the distal lip.

In an aspect, the annular seal is disposed within the inner annular region of the seal retainer.

In an aspect, the annular seal includes an outer surface having a proximal lip and a distal lip extending radially outwardly from the outer surface of the annular seal.

In an aspect, the proximal lip and the distal lip of the annular seal are disposed within the inner annular region of the seal retainer to prevent axial movement of the annular seal as the trocar moves through the inner opening of the annular seal.

In an aspect, the annular seal includes a recessed region defined between the proximal lip of the annular seal and the distal lip of the annular seal. The proximal lip of the annular seal may be disposed within the inner annular region of the seal retainer and the distal lip of the seal retainer may be disposed within the recessed region of the annular seal to prevent axial movement of the annular seal as the trocar moves through the inner opening of the annular seal.

In an aspect, the elongate body portion has an outer surface defining a non-circular shape and the inner opening of the annular seal is dimensioned to correspond in shape to the non-circular shape of the outer surface of the elongate body portion.

In an aspect, the annular seal is formed of an elastomeric material configured to compress when the trocar is positioned through the inner opening of the annular seal.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

Various aspects of the disclosure are described herein below with reference to the drawings, wherein:

FIG. 2 is a perspective view of an adaptor assembly of the circular stapling device of FIG. 1;

FIG. 3 is a side view of a trocar assembly usable with the adaptor assembly of FIG. 2;

FIG. 4 is a partial exploded view of the trocar assembly of FIG. 3;

FIG. 5 is an enlarged view of the indicated area of detail shown in FIG. 4 including an annular seal of the trocar assembly of FIG. 3;

FIG. 6 is a side cross-sectional view of a distal portion of the adaptor assembly of FIG. 2 taken along section line 6-6;

FIG. 7 is an enlarged view of the indicated area of detail shown in FIG. 6 including the annular seal and a seal retainer of the trocar assembly of FIG. 3;

FIG. 10 is a side cross-sectional view of the trocar assembly of FIG. 8 taken along section line 10-10; and FIG. 11 is an enlarged view of the indicated area of detail shown in FIG. 10 including the annular seal and a seal retainer of the trocar assembly of FIG. 8.

DETAILED DESCRIPTION

In this description, the term "proximal" is used generally to refer to that portion of the device that is closer to a clinician, while the term "distal" is used generally to refer to that portion of the device that is farther from the clinician. Further, the term "clinician" is used generally to refer to medical personnel including doctors, nurses, and support personnel.

The aspects of the disclosed trocar assembly and stapling device utilizing the disclosed trocar assembly provide one or more seals that prevent fluid ingress into components of the trocar assembly and stapling device. The powered circular stapling device adaptor is a reusable device that is designed to be cleaned and used again in several procedures. Because tissue, fluids, contaminants, and other biological matter can enter the device through a distal opening in the adaptor assembly and, in particular, about the trocar assembly, it is necessary to clean inside the adaptor assembly and its components prior to reuse. To assist with this cleaning, a trocar of the adaptor is removed prior to cleaning to allow greater access to the interior of the adaptor. Properly removing and reattaching the trocar can present challenges to clinicians and have a detrimental effect on the reliability of the stapling device.

The disclosure describes a powered, or non-powered, circular stapling device (or other applicable medical devices) that incorporates a seal in the trocar assembly to prevent fluid ingress into the device and components of the device including the adaptor assembly. The seal or seals can combine to create a barrier to entry of bodily soils to the interior of the device.

In accordance with this disclosure, a trocar assembly can be fixed to an adaptor assembly while the adaptor assembly is cleaned, thereby reducing the burden for clinicians to assemble and disassemble the device, cost, and potential for error. By placing one or more seals in the trocar assembly, the adaptor assembly can be less complex and still allow the device to be cleaned should any small amount of soil get past the seals.

Figure 1:
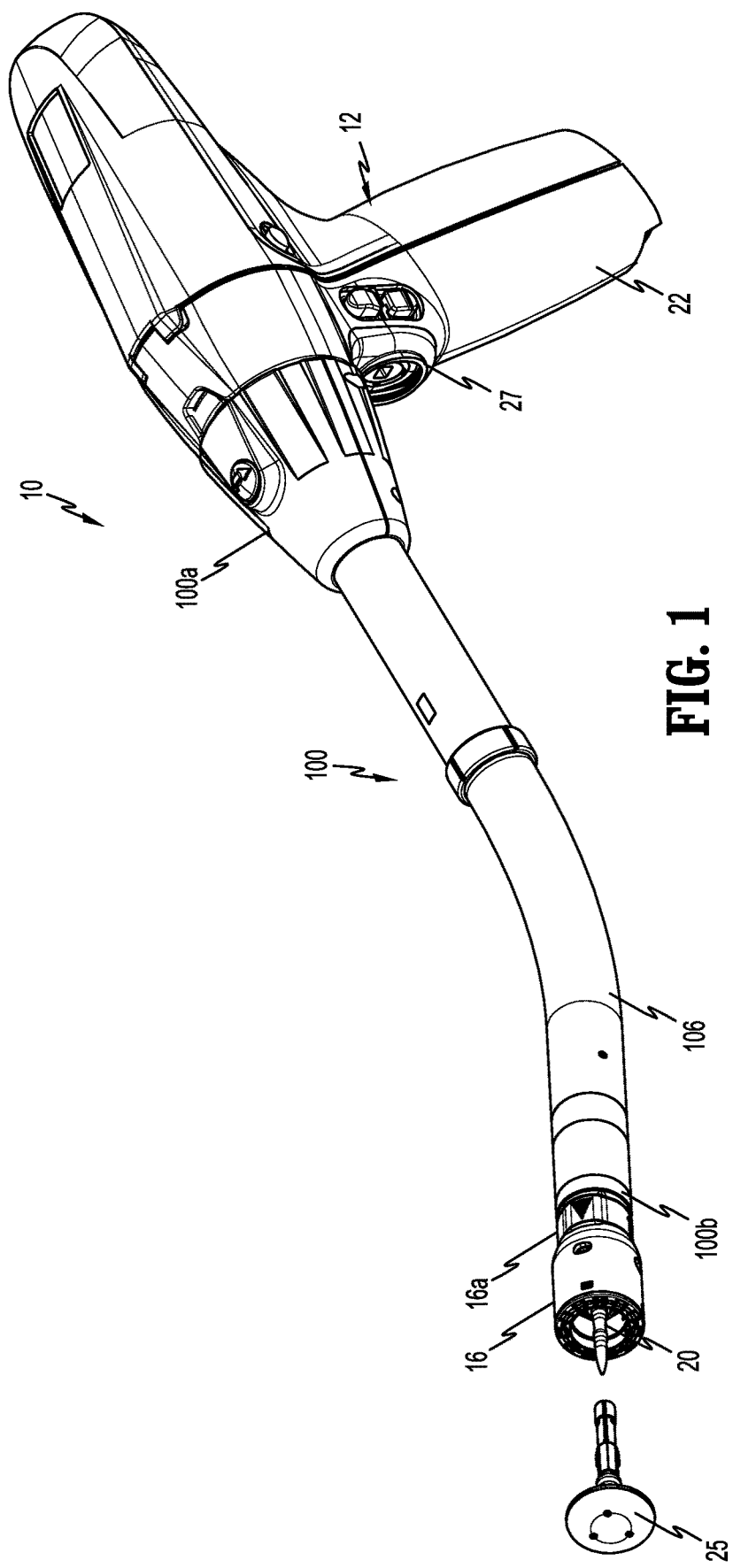
FIG. 1 is a perspective view of a circular stapling device including aspects of the disclosure.
Figure 8:
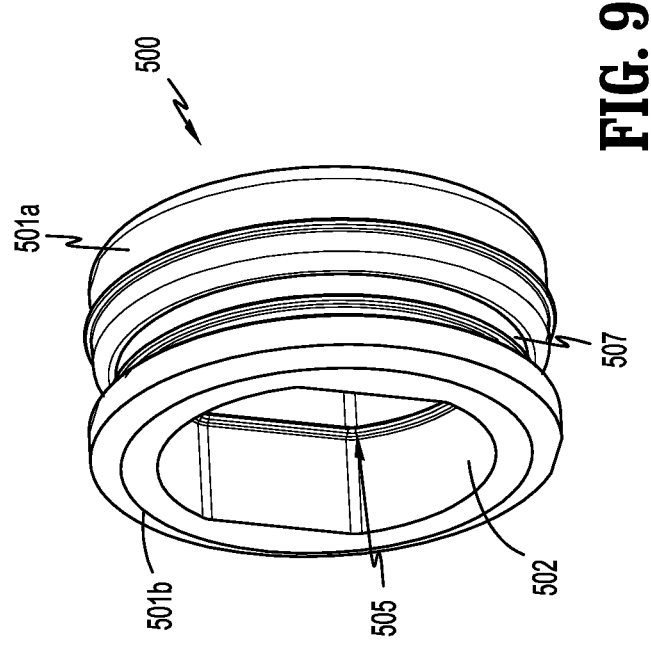
FIG. 8 is a perspective view of another trocar assembly including other aspects of the disclosure usable with the adaptor assembly of FIG. 2.

FIG. 1 illustrates a circular stapling device 10 including a handle assembly 12, an elongate body or adaptor assembly 100, a reload assembly 16 releasably supported on the adaptor assembly 100, and an anvil assembly 25 releasably supported for movement in relation to the reload assembly 16 between an open position and a clamped position.

The reload assembly 16 includes a proximal portion 16a that can be releasably coupled to a distal portion 100b of the adaptor assembly 100 and the adaptor assembly 100 includes a proximal portion 100a that can be releasably coupled to the handle assembly 12. The handle assembly 12 includes a stationary grip 22 that supports actuation buttons 27 for controlling operation of various functions of the circular stapling device 10 including approximation of the reload assembly 16 and anvil assembly 25, firing of staples from the reload assembly 16, and cutting or coring of tissue.

The circular stapling device 10 is illustrated as an electrically powered stapling device including an electrically powered handle assembly 12 that may support one or more batteries (not shown). The adaptor assembly 100 translates power from the handle assembly 12 to the reload and anvil assemblies 16, 25, respectively, to staple and cut tissue. It is envisioned that the disclosed aspects could also be incorporated into a stapling device that is configured for use with a robotic system that does not include a handle assembly, or to a stapling device including a manually actuated handle assembly.

Figure 9:
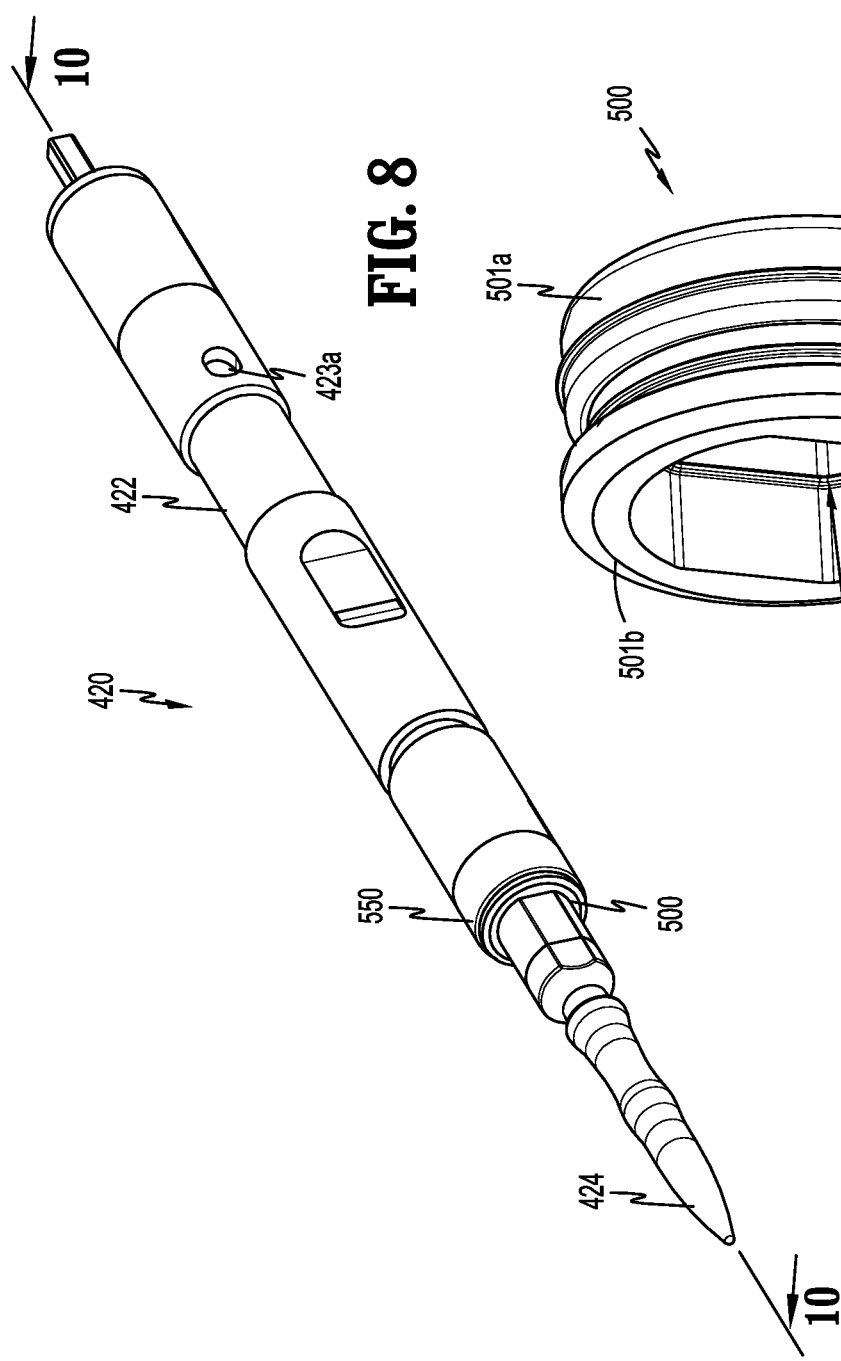
FIG. 9 is a perspective view of an annular seal of the trocar assembly of FIG. 8.

In certain aspects of the disclosure, the reload assembly 16 of the circular stapling device 10 is designed to be disposable and the handle assembly 12 and the adaptor assembly 100 are designed to be reprocessed or resterilized and reused. As such, the reload assembly 16 and components that form the reload assembly 16 are formed of materials, e.g., plastics, that are less costly and less durable than materials e.g., stainless steel, used to form the handle assembly 12 and/or the adaptor assembly 100. Additionally, prevention of contaminant ingress into the reusable components of the circular stapling device 10, such as the handle assembly 12 and the adaptor assembly 100, simplifies the sterilization process for these reusable components. In aspects of the disclosure, the adaptor assembly 100, and in particular, the trocar assembly 20 of the adaptor assembly 100 includes a seal (e.g., annular seal 300 of FIG. 5 or annular seal 500 of FIG. 9) to prevent the ingress of contaminants into and about the trocar assembly 20 and the adaptor assembly 100.

FIG. 2 illustrates a trocar assembly 20 received within the distal portion 100b of the adaptor assembly 100 and configured to operably engage the anvil assembly 25 (FIG. 1). In aspects, the trocar assembly 20 is fixedly coupled to the adaptor assembly 100 and not removable therefrom. Alternatively, the trocar assembly 20 may be removably coupled to the adaptor assembly 100. A first aspect of the trocar assembly 20 is described as a trocar assembly 120 (FIGS. 3-7) and a second aspect of the trocar assembly 20 is described as a trocar assembly 420 (FIGS. 8-11). Throughout this description, the trocar assembly 120 and the trocar assembly 420 are referred to collectively as trocar assembly 20.

FIGS. 3-7 illustrate the trocar assembly 120 of the adaptor assembly 100 (FIG. 2) which includes a trocar housing 122, a trocar 123, a drive screw 126, an annular seal 300, and a seal retainer 350. The trocar 123 includes a trocar member 124, an elongate body portion 125, and a nut 129 having a threaded inner surface. The elongate body portion 125 extends distally from the nut 129. The trocar member 124 extends distally from the elongate body portion 125 and defines a tapered tip that is configured to pierce tissue. The trocar 123, which extends through the annular seal 300, is movably disposed within the trocar housing 122 and is movable relative to the trocar housing 122 via rotation of the drive screw 126. The trocar housing 122 defines first and second retaining elements 123a, 123b for coupling the trocar housing 122 to the adaptor assembly 100 (FIG. 2) and preventing rotation of the trocar housing 122 within the adaptor assembly 100 as the drive screw 126 is rotated.

The drive screw 126 is operably received within a hollow portion of the elongate body portion 125 of the trocar 123 and is threadingly engaged with the threaded inner surface of the nut 129 of the trocar 123 for axially moving the trocar 123 relative to the trocar housing 122. In particular, rotation of the drive screw 126 effects axial movement of the nut 129 and the elongate body portion 125, and in turn, the trocar member 124 disposed at the distal end of the elongate body portion 125, along a longitudinal axis, relative to the trocar housing 122. The elongate body portion 125 may be rotatably fixed to the nut 129, to form a single unitary component, such that rotation of the nut 129 effects rotation of the elongate body portion 125 in addition to effecting axial movement of the elongate body portion 125.

The annular seal 300 has an inner annular surface 302 defining an inner opening 305 and is retained to the trocar housing 122 by the seal retainer 350. The inner opening 305 of the annular seal 300 is sized and dimensioned to correspond in shape and size of the elongate body portion 125 of the trocar 123. The inner annular surface 302 of the annular seal 300 is frictionally engaged to the elongate body portion 125 of the trocar 123 to form a fluid-tight seal between the annular seal 300 and the trocar 123 (e.g., an outer surface of the trocar 123) when the trocar 123 is positioned through the inner opening 305 of the annular seal 300. The seal retainer 350 is fixedly coupled to the trocar housing 122, for example at a distal end 122b of the trocar housing 122, and defines an inner annular region 352 (as described below) that receives the annular seal 300. The seal retainer 350 may be coupled to the trocar housing 122 via welding, press-fit engagement, threaded coupling, as a separate component, or may be machined into the distal end 122b of the trocar housing 122 as a single unitary component.

FIGS. 6 and 7 illustrate the fluid-tight seal formed between the annular seal 300 and the outer surface of the elongate body portion 125 of the trocar 123. Such a fluid-tight seal formed by the annular seal 300 prevents contaminants from entering into the components of the trocar assembly 120 and in turn, other portions of the adaptor assembly 100. The seal retainer 350 includes a proximal lip 351a and a distal lip 351b that define the inner annular region 352 between the proximal lip 351a and the distal lip 351b. The annular seal 300 is disposed, partially or entirely, within the inner annular region 352 of the seal retainer 350 to prevent axial movement of the annular seal 300 as the trocar 123 moves through the inner opening 305 of the annular seal 300.

In an aspect, the annular seal 300 (FIG. 5) includes a proximal lip 301a and a distal lip 301b extending radially outward from the outer surface of the annular seal 300 and radially inward from the inner annular surface 302 of the annular seal 300. The proximal lip 301a and the distal lip 301b of the annular seal 300 provide a more effective seal between the annular seal 300 and the trocar 123 and the annular seal 300 and the seal retainer 350.

The annular seal 300 may be formed of an elastomeric material such as rubber or other compressible or flexible material. The inner opening 305 of the annular seal 300 is dimensioned such that when the trocar 123 is positioned through the inner opening 305, the trocar 123 forces the annular seal 300 outwardly to compress against the seal retainer 350 against which the annular seal 300 rests. Thus, in an aspect, when the annular seal 300 is in a relaxed (e.g., non-flexed or non-compressed) condition, the diameter of the inner opening 305 of the annular seal 300 is equal to, or less than, the outer diameter of the elongate body portion 125 of the trocar 123.

FIGS. 8-11 illustrate alternative aspects of the disclosed trocar assembly 20 shown generally as trocar assembly 420, which includes a trocar housing 422, a trocar 423, a drive screw 426, an annular seal 500, and a seal retainer 550. The trocar 423 includes a trocar member 424 and an elongate body portion 425. The trocar member 424 extends distally from the elongate body portion 425 and defines a tapered tip that is configured to pierce tissue. The elongate body portion 425 includes a threaded portion 425t defined along its inner surface. The trocar 123, which extends through the annular seal 500, is movably disposed within the trocar housing 422 and is movable relative to the trocar housing 422 via rotation of the drive screw 426. The trocar housing 422 defines a retaining element 423a for coupling the trocar housing 422 to the adaptor assembly 100 (FIG. 2) and preventing rotation of the trocar housing 422 within the adaptor assembly 100 as the drive screw 126 is rotated.

The drive screw 426 is operably received within a hollow portion of the elongate body portion 425 of the trocar 423 and is threadingly engaged with the threaded portion 425t of the elongate body portion 425 of the trocar 423 for axially moving the trocar 423 relative to the trocar housing 422. In particular, rotation of the drive screw 426 effects axial movement of the elongate body portion 425, and in turn, the trocar member 424 disposed at the distal end of the elongate body portion 425, along a longitudinal axis, relative to the trocar housing 422.

The annular seal 500 has an inner annular surface 502 defining an inner opening 505 and is retained to the trocar housing 422 by the seal retainer 550. The inner opening 505 of the annular seal 500 is sized and dimensioned to correspond in shape and size of the elongate body portion 425 of the trocar 423. The inner annular surface 502 of the annular seal 500 is frictionally engaged to the elongate body portion 425 of the trocar 423 to form a fluid-tight seal between the annular seal 500 and the trocar 423 (e.g., an outer surface of the trocar 423) when the trocar 423 is positioned through the inner opening 505 of the annular seal 500. The seal retainer 550 is fixedly coupled to the trocar housing 422, for example at a distal end 422b of the trocar housing 422, and defines an inner annular region 552 (as described below) that receives a portion of the annular seal 500. The seal retainer 550 may be coupled to the trocar housing 422 via welding, press-fit engagement, threaded coupling, as a separate component, or may be machined into the distal end 422b of the trocar housing 422 as a single unitary component.

FIGS. 10 and 11 illustrate the fluid-tight seal formed between the annular seal 500 and the outer surface of the elongate body portion 425 of the trocar 423. Such a fluid-tight seal formed by the annular seal 500 prevents contaminants from entering into the components of the trocar assembly 420 and in turn, other portions of the adaptor assembly 100. The seal retainer 550 includes a proximal lip 551a and a distal lip 551b that define the inner annular region 552 between the proximal lip 551a and the distal lip 551b. A portion of the annular seal 500 is disposed within the inner annular region 552 of the seal retainer 550 to prevent axial movement of the annular seal 500 as the trocar 423 moves through the inner opening 505 of the annular seal 500. In particular, the annular seal 500 includes a proximal lip 501a and a distal lip 501b extending radially outward from the outer surface of the annular seal 500 which define a recessed region 507 between the proximal lip 501a and the distal lip 501b. The proximal lip 501a of the annular seal 500 is disposed within the inner annular region 552 of the seal retainer 550 and the distal lip 551b of the seal retainer 550 is disposed within the recessed region 507 of the annular seal 500 to secure the annular seal 500 to the seal retainer 550 and provide a more effective seal between the annular seal 500 and the seal retainer 550 and to prevent axial movement of the annular seal 500 as the trocar 423 moves through the inner opening 505 of the annular seal 500.

Similar to the annular seal 300 (described above), the annular seal 500 may be formed of an elastomeric material such as rubber or other compressible, or flexible material. The inner opening 505 of the annular seal 500 is dimensioned such that when the trocar 423 is positioned through the inner opening 505, the trocar 423 forces the annular seal 500 outwardly to compress against the seal retainer 550 against which the annular seal 500 rests. Thus, in an aspect, when the annular seal 500 is in a relaxed (e.g., non-flexed or non-compressed) condition, the diameter of the inner opening 505 of the annular seal 500 is equal to, or less than, the outer diameter of the elongate body portion 425 of the trocar 423.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A stapling device comprising:
a handle assembly;
an adaptor assembly extending from the handle assembly, and including a trocar assembly, the trocar assembly including:
a trocar housing including an inner surface defining a lumen;
an annular seal positioned within the lumen of the trocar housing, the annular seal having an inner annular surface defining an inner opening;
a trocar disposed within the lumen of the trocar housing, extending through the inner opening of the annular seal, and movable through the lumen of the trocar housing and the inner opening of the annular seal, the trocar including an elongate body portion having a distal end and a trocar member extending distally from the distal end of the elongate body portion; and
a seal retainer operably coupled to the trocar housing, the seal retainer positioned to retain the annular seal within the lumen of the trocar housing.

2. The stapling device of claim 1, wherein the inner annular surface of the annular seal is frictionally engaged to the elongate body portion of the trocar to form a fluid-tight seal between the annular seal and the trocar.

3. The stapling device of claim 1, wherein the seal retainer is fixedly coupled to the trocar housing.

4. The stapling device of claim 3, wherein the trocar housing has a distal end and the seal retainer has a proximal end, the proximal end of the seal retainer being secured to the distal end of the trocar housing.

5. The stapling device of claim 1, wherein the seal retainer includes a proximal lip and a distal lip and defines an inner annular region between the proximal lip and the distal lip.

6. The stapling device of claim 5, wherein the annular seal is disposed within the inner annular region of the seal retainer.

7. The stapling device of claim 5, wherein the annular seal includes an outer surface including a proximal lip and a distal lip, the proximal lip and the distal lip of the outer surface of the annular seal extending radially outwardly from the outer surface of the annular seal.

8. The stapling device of claim 7, wherein the proximal lip and the distal lip of the annular seal are disposed within the inner annular region of the seal retainer to prevent axial movement of the annular seal as the trocar moves through the inner opening of the annular seal.

9. The stapling device of claim 7, wherein the annular seal includes a recessed region defined between the proximal lip of the annular seal and the distal lip of the annular seal, the proximal lip of the annular seal disposed within the inner annular region of the seal retainer and the distal lip of the seal retainer disposed within the recessed region of the annular seal.

10. A trocar assembly comprising:
a trocar housing including an inner surface defining a lumen;
an annular seal positioned within the lumen of the trocar housing, the annular seal having an inner annular surface defining an inner opening;

a trocar disposed within the lumen of the trocar housing, extending through the inner opening of the annular seal, and movable through the lumen of the trocar housing and the inner opening of the annular seal, the trocar including an elongate body portion having a distal end and a trocar member extending distally from the distal end of the elongate body portion; and a seal retainer operably coupled to the trocar housing, the seal retainer positioned to retain the annular seal within the lumen of the trocar housing, wherein the elongate body portion has an outer surface defining a non-circular shape and the inner opening of the annular seal is dimensioned to correspond in shape to the non-circular shape of the outer surface of the elongate body portion.

11. The trocar assembly of claim 10, wherein the inner annular surface of the annular seal is frictionally engaged to the elongate body portion of the trocar to form a fluid-tight seal between the annular seal and the trocar.

12. The trocar assembly of claim 10, wherein the seal retainer is fixedly coupled to the trocar housing.

13. The trocar assembly of claim 12, wherein the trocar housing has a distal end and the seal retainer has a proximal end, the proximal end of the seal retainer being secured to the distal end of the trocar housing.

14. The trocar assembly of claim 10, wherein the seal retainer includes a proximal lip and a distal lip and defines an inner annular region between the proximal lip and the distal lip.

15. The trocar assembly of claim 14, wherein the annular seal is disposed within the inner annular region of the seal retainer.

16. The trocar assembly of claim 14, wherein the annular seal includes an outer surface having a proximal lip and a distal lip, the proximal lip and the distal lip of the outer surface of the annular seal extending radially outwardly from the outer surface of the annular seal.

17. The trocar assembly of claim 16, wherein the proximal lip and the distal lip of the annular seal are disposed within the inner annular region of the seal retainer to prevent axial movement of the annular seal as the trocar moves through the inner opening of the annular seal.

18. The trocar assembly of claim 16, wherein the annular seal includes a recessed region defined between the proximal lip of the annular seal and the distal lip of the annular seal, the proximal lip of the annular seal disposed within the inner annular region of the seal retainer and the distal lip of the seal retainer disposed within the recessed region of the annular seal.

19. The trocar assembly of claim 10, wherein the annular seal is formed of an elastomeric material configured to compress when the trocar is positioned through the inner opening of the annular seal.

20. A trocar assembly comprising:

a trocar housing including an inner surface defining a lumen;

an annular seal positioned within the lumen of the trocar housing, the annular seal having an inner annular surface defining an inner opening;

a trocar disposed within the lumen of the trocar housing, extending through the inner opening of the annular seal, and movable through the lumen of the trocar housing and the inner opening of the annular seal, the trocar including an elongate body portion having a distal end and a trocar member extending distally from the distal end of the elongate body portion; and a seal retainer operably coupled to the trocar housing, the seal retainer positioned to retain the annular seal within the lumen of the trocar housing, wherein the trocar housing has a distal end and the seal retainer has a proximal end, the proximal end of the seal retainer being secured to the distal end of the trocar housing.

\* \* \* \* \*